United States Patent [19]

Grimard

[11] Patent Number: 5,308,330

[45] Date of Patent: May 3, 1994

[54] SYRINGE HAVING NEEDLE ISOLATION FEATURES

[75] Inventor: Jean P. Grimard, Vif, France

[73] Assignee: Becton, Dickinson and Company, Franklin Lakes, N.J.

[21] Appl. No.: 945,796

[22] Filed: Sep. 16, 1992

[51] Int. Cl.⁵ ............................................. A61M 5/00
[52] U.S. Cl. ..................................... 604/110; 604/218
[58] Field of Search ............ 604/110, 187, 218, 246, 604/247, 82, 89, 91

[56] References Cited

U.S. PATENT DOCUMENTS

| | | | |
|---|---|---|---|
| 2,323,159 | 6/1943 | Smith | 604/91 |
| 4,116,240 | 9/1978 | Guiney | 604/89 |
| 4,952,206 | 8/1990 | Ibanez et al. | 604/110 |
| 5,026,346 | 6/1991 | Spanner et al. | 604/218 |

FOREIGN PATENT DOCUMENTS 7615 of 1913 United Kingdom .................. 604/82

*Primary Examiner*—John D. Yasko
*Attorney, Agent, or Firm*—John L. Voellmicke

[57] ABSTRACT

A syringe having structure to isolate fluid from the distal end of the syringe includes a barrel with a chamber therein. A stopper is slidingly disposed in the chamber and is provided with an aperture extending axially therethrough. A plug includes a head releasably engaged in a sealing portion of the aperture of the stopper. A rigid tail extends distally from the head and through the aperture in the stopper and projects outwardly from the distal end of the stopper. The tail is long enough so that it can be used to move the head out of the sealing portion of the aperture by applying force to the distal end of the tail. The tail has a cross-sectional shape which defines at least one fluid channel between the tail and the sealing portion of the stopper to allow fluid to flow from the chamber through the aperture in the stopper and out of the distal end of the barrel.

17 Claims, 5 Drawing Sheets

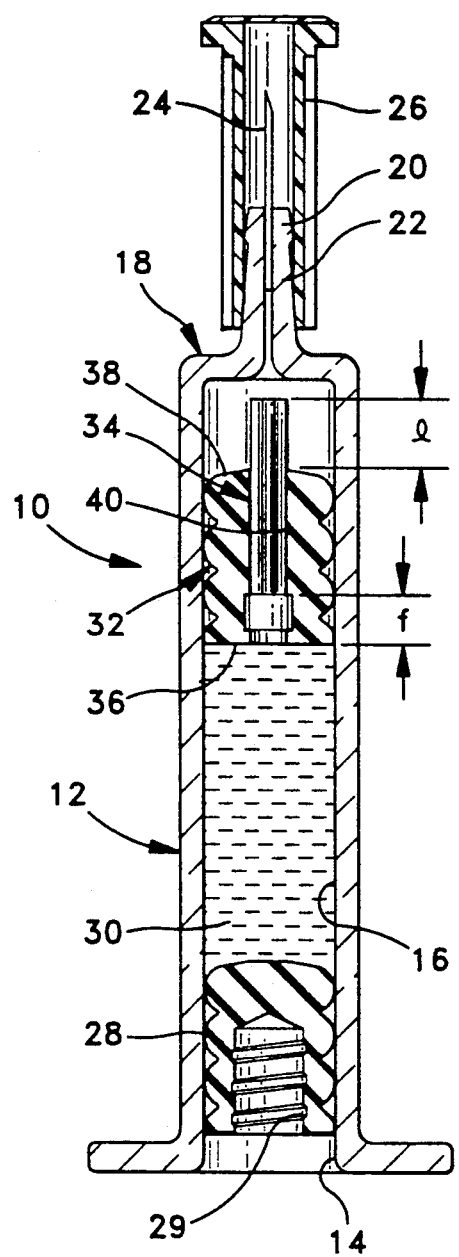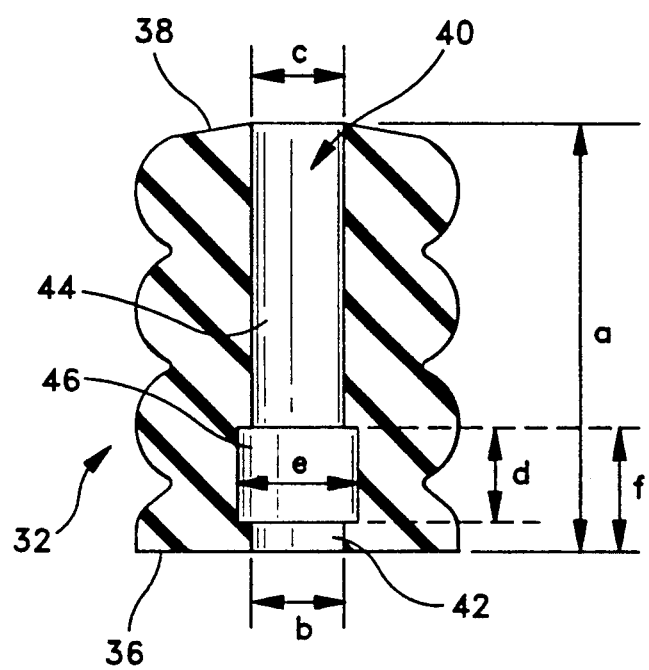

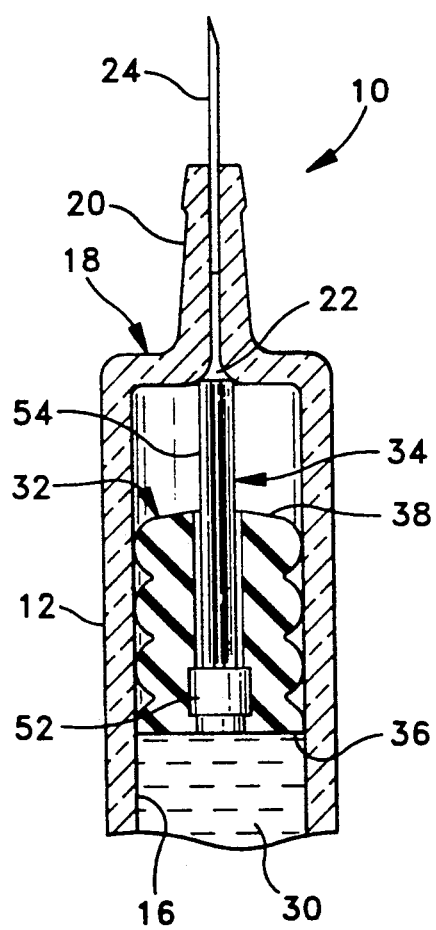
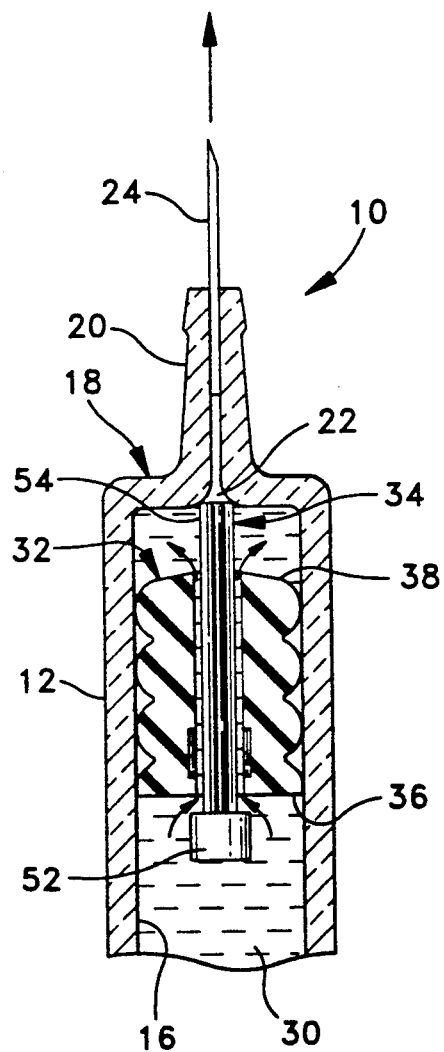

5,308,330

SYRINGE HAVING NEEDLE ISOLATION FEATURES

BACKGROUND OF THE INVENTION

1. Field of the Invention

The present invention relates to syringes and more particularly concerns a syringe suitable for prefilling including structure for preventing the contents of the syringe from exiting the needle end of the syringe barrel during storage.

2. Description of the Prior Art

Prior art hypodermic syringes include an elongated barrel having opposed proximal and distal ends and a chamber therebetween for receiving a fluid. A passageway extends through the distal end of the syringe barrel and communicates with the chamber. The distal end of the prior art syringe barrel is connected to a sharp needle cannula for delivering fluid from the chamber and passageway. The proximal end of the prior art syringe barrel slidably receives a plunger, such that movement of the plunger urges fluid through the needle cannula.

Many prior art hypodermic syringes are prefilled with fluid prior to shipment to health care facilities or other end users. Prefilling of a hypodermic syringe offers several advantages. In particular, handling of the hypodermic syringe after removal of the protective needle shield is substantially reduced. Additionally, required dosages can be carefully controlled to avoid misuse of the fluid being injected. Still further, inventory management at the health care facility can be simplified.

Contact between the prefilled fluid and the needle cannula or the passageway through the distal end of the prior art syringe barrel can cause clogging, leakage, and in some areas, possible chemical interaction between the needle and the fluid. Thus, in some cases it is desirable to isolate the prefilled fluid from the distal end of the syringe barrel and from the needle.

The prior art has included several structures for isolating the fluid in the prefilled hypodermic syringe and the distal end of the barrel. One prior art approach has included a rupturable membrane mounted at a distal location within the syringe barrel to separate the prefilled fluid from the needle and syringe tip. Slidable movement of the plunger in this prior art syringe barrel causes the prefilled fluid to increase pressure on the membrane. Sufficient pressure causes the membrane to either rupture or to deform into an inner needle which pierces the membrane. Further slidable movement of the plunger into the prior art syringe barrel causes the prefilled fluid to pass through the ruptured or pierced membrane and into the needle cannula. This prior art approach, however, creates the potential that a portion of the membrane could disengage and either block the needle cannula or pass entirely therethrough.

Other prior art prefilled hypodermic syringes have included a syringe barrel with an enlarged cross section near the distal end. A stopper is slidably disposed in the syringe barrel proximally of the enlarged cross-section to isolate the prefilled fluid from both the needle and the enlarged cross-sectional region of the barrel. Slidable movement of the plunger into this prior art syringe barrel moves the stopper distally and into the region of enlarged cross-section. The fluid then bypasses the stopper and flows into the needle cannula. The non-uniform cross-section along the length of this prior art syringe barrel can complicate manufacturing processes and increase manufacturing costs.

Still other prior art syringes have included isolation stoppers which deform, when they reach the distal end of the barrel, in response to the increased pressure of the fluid generated by the slidable movement of the plunger. Prior art devices of this type may require uncertain or excessive pressure on the plunger and require a higher pressure throughout the injection process because they close the fluid path to the needle when the pressure is reduced.

SUMMARY OF THE INVENTION

The subject invention is directed to a syringe with a syringe barrel having opposed distal and proximal ends and a chamber extending therebetween. Portions of the syringe barrel between the proximal and distal ends may be of substantially uniform cross-section. The distal end of the syringe barrel defines a tip with a passageway extending therethrough and communicating with the chamber, and a needle cannula may be removably or permanently connected to the tip. The proximal end of the syringe barrel is opened for receiving both a fluid to be injected and a plunger.

A stopper is mounted in sliding fluid-tight engagement in the syringe barrel. The stopper has opposed proximal and distal ends and at least one aperture extending therethrough. The aperture may be parallel to or coincident with the axis of the syringe barrel. The aperture through the stopper may be of substantially constant cross-section along its length. Alternatively, the aperture may be characterized by a seat or sealing portion of enlarged or reduced, increased, cross-section along a portion of the length of the aperture or along the entire length of the aperture.

The syringe of the subject invention further includes at least one elongate plug releasably engaged in the aperture of the stopper. The plug includes opposed proximal and distal ends. The plug includes a head which is dimensioned and configured to be releasably engaged in the aperture of the stopper. More particularly, the head of the plug may be dimensioned to be releasably engaged in the above-described seat or sealing portion of the aperture in the stopper.

The plug further includes a tail extending distally from the head. The tail defines an axial length which is usually greater than the axial length of the sealing portion of the aperture through the stopper, and a cross-sectional area preferably less than the cross-sectional area of the aperture through the stopper. The tail may have a variety of shapes including fluted or other cylindrical or non-cylindrical exterior surface to define at least one longitudinally extending fluid channel along the length of the interface between the sealing portions and the tail. The longitudinally extending channel may follow a helical path along the exterior of the plug.

The hypodermic syringe of the subject invention may be assembled by inserting the plug into the aperture of the stopper such that the tail of the plug projects beyond the distal end of the stopper, and such that the head of the plug is releasably engaged by the sealing portion of the aperture in the stopper. The combined plug and stopper are then slidably inserted into the open proximal end of the syringe barrel with the tail of the plug projecting distally in the syringe barrel. The stopper engages both the interior surfaces of the syringe barrel and the plug. Thus, the stopper and the plug effectively isolate a proximal portion of the chamber in the syringe barrel from the tip and needle at the distal end of the syringe barrel. A fluid may then be prefilled into the proximal end of the syringe barrel, and may be retained and further isolated therein by the plunger.

The hypodermic syringe may be used by slidably advancing the plunger distally into the syringe barrel. The distal movement of the plunger exerts a pressure on the fluid and causes simultaneous slidable movement of both the stopper and plug in the syringe barrel. Sufficient distal movement of the plug and stopper bringing the distal end of the plug tail into contact with the distal end of the syringe barrel. Thus, further distal movement of the plug is prevented, and additional advancement of the plunger causes distal movement of the stopper independent of the plug. Sufficient movement of the stopper relative to the plug will cause sealing portion of the aperture of the the stopper to disengage from the head of the plug. In this relative orientation, the fluid in the chamber flows around the tail of the plug and through the aperture of the stopper.

The subject hypodermic syringe is desirable in that it does not require a specially manufactured syringe barrel or plunger. Additionally, the subject hypodermic syringe does not require a rupturable membrane nor a resilient stopper/valve. Rather, the hypodermic syringe of the subject invention relies upon the efficient and highly predictable movement of the stopper relative to the plug.

BRIEF DESCRIPTION OF THE DRAWINGS

FIG. 2 is a cross-sectional view taken along line 2—2 in FIG. 1;

FIG. 3 is a cross-sectional view of the stopper shown in FIGS. 1 and 2;

FIG. 9 is a partial cross-sectional view similar to FIG. 2, with the stopper and plug moved distally into the syringe barrel;

FIG. 10 is a partial cross-sectional view similar to FIGS. 2 and 9, showing the stopper moved distally further into the syringe barrel;

DETAILED DESCRIPTION OF THE PREFERRED EMBODIMENT

Figure 1:
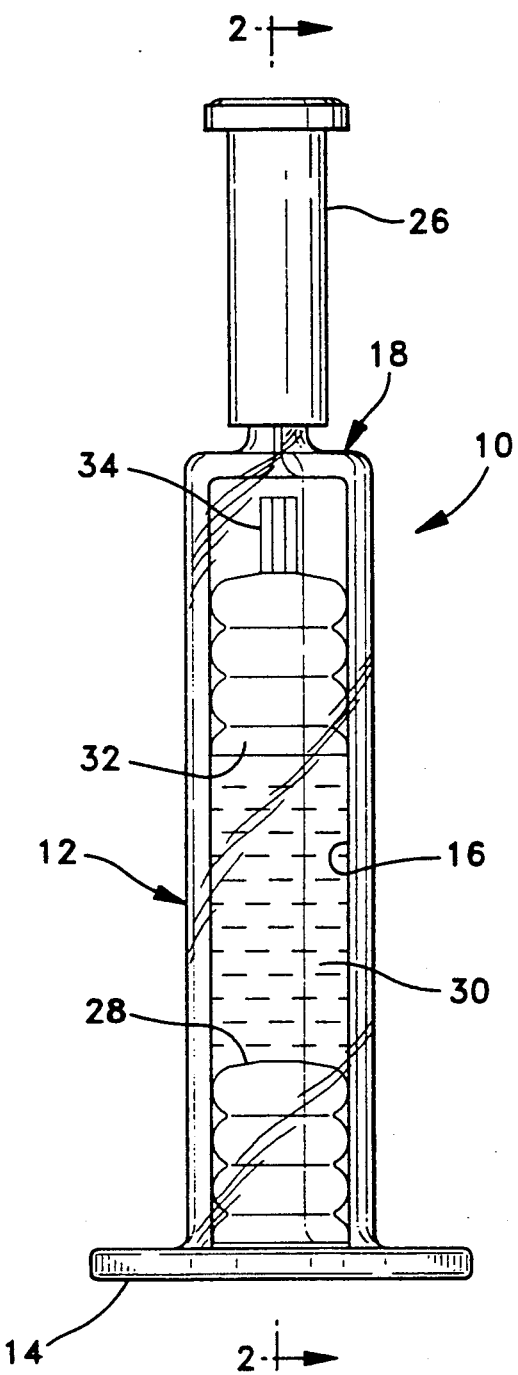
FIG. 1 is a side elevational view of a hypodermic syringe in accordance with the subject invention.

A hypodermic syringe in accordance with the subject invention is identified generally by the numeral 10 in FIGS. 1 and 2. Hypodermic syringe 10 includes a generally cylindrical syringe barrel 12 formed from a rigid material which is preferably transparent glass or thermoplastic material. Barrel 12 includes an open proximal end 14 which leads into a fluid-receiving cylindrical chamber 16. Barrel 12 further includes a distal end identified generally by the numeral 18. Distal end 18 includes a tip 20 with a passageway 22 extending therethrough and communicating with the chamber 16. In this preferred embodiment a hollow needle cannula 24 is securely mounted to the tip 20 of the syringe barrel 12 and communicates with the passageway 22. The hypodermic syringe 10 is further provided with a needle shield 26 releasably engaged around tip 20 of the syringe barrel for enclosing and isolating the needle. It is also within the purview of the invention to include a syringe barrel without a needle cannula and a syringe barrel having a needle assembly which is removably attached.

For the purposes of the description of the present invention, the term "distal end" is meant to refer to the end furthest from the person holding the syringe or closest to the needle end or discharge end of the syringe, whereas the term "proximal end" is meant to refer to the end closest to the holder of the syringe and furthest from the needle end or discharge end of the syringe.

The chamber 16 of the syringe barrel 12 receives a plunger stopper or plunger 28 in sliding fluid-tight engagement with barrel 12. Plunger 28 can be slid through chamber 16 of barrel 12 from proximal end 14 toward distal end 18 to expel a fluid 30 through passageway 22 in the tip and through needle cannula 24 Movement of the plunger stopper or plunger 28 is accomplished by applying force to a rigid plunger rod (not shown) which attaches to plunger 28 and extends outwardly from proximal end 14 of the barrel. In this embodiment the plunger 28 includes internal threaded recess 29 for engaging a rigid plunger rod having a distal threaded portion (not shown).

Hypodermic syringe 10 is preferably intended to be prefilled with fluid 30 that will be injected through the needle cannula. As noted above, it is desirable to isolate needle 24 and passageway 22 from the fluid until the fluid is about to be injected. To achieve this isolation, syringe 10 includes an isolation stopper or stopper 32 and a plug 34 disposed in chamber 16 distally of plunger 28. Stopper 32 is preferably formed from resilient material such as rubber and thermoplastic elastomers and has an exterior surface dimensioned and configured to be in sliding fluid-tight engagement with barrel 12. It should be noted that the plunger and stopper of this invention can be made resilient through design configuration as well as by using resilient materials. Stopper 32 includes a proximal end 36, an opposed distal end 38 and an aperture 40 extending axially therebetween. Aperture 40, in this embodiment, defines a total axial length "a" as shown in FIG. 3. The aperture is characterized by small diameter regions 42 and 44 adjacent the proximal and distal ends 36 and 38 respectively. Small diameter regions 42 and 44 define diameters "b" and "c", which preferably are equal to one another. Aperture 40 is further characterized by a seat 46 intermediate the small diameter regions 42 and 44. Seat 46 defines a length "d" and a diameter "e" which, in this embodiment, is greater than diameters "b" and "c". The distal end of seat 46 is spaced from proximal end 36 of stopper 32 by a distance "f".

A plug 34 is illustrated in greatest detail in FIGS. 4–7. Plug 34 is formed from a substantially rigid material such as thermoplastic material or hard rubber, and includes opposed proximal and distal ends 48 and 50. A head 52 extends distally from proximal end 48 of plug 34 for an axial distance "g", which is approximately equal to axial length "d" of seat 46 in stopper 32. Head 52 of plug 34 defines a diameter "h" which is approximately equal to or slightly greater than diameter "e" of seat 46 in stopper 32. Thus, as explained further herein, head 52 of plug 34 can be releasably engaged in seat 46 of aperture 40 due to the resiliency of the resilient material of stopper 32.

Figure 4:
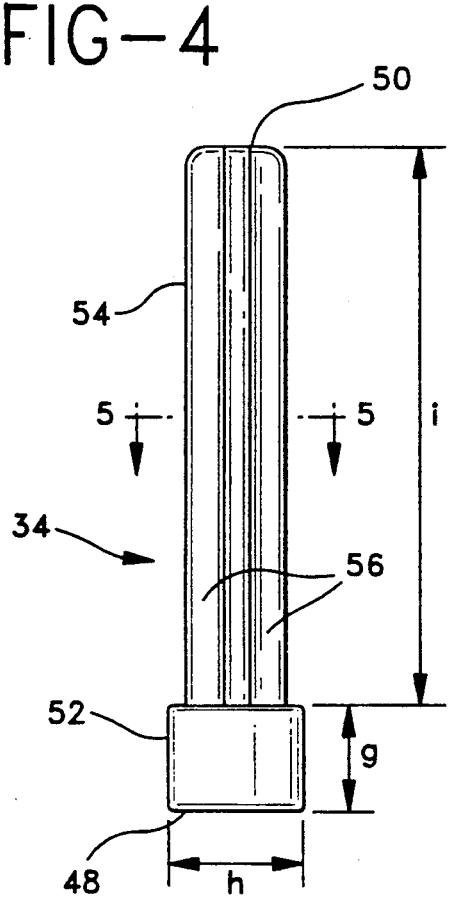
FIG. 4 is a side elevational view of the plug shown in FIGS. 1 and 2.
Figure 5:
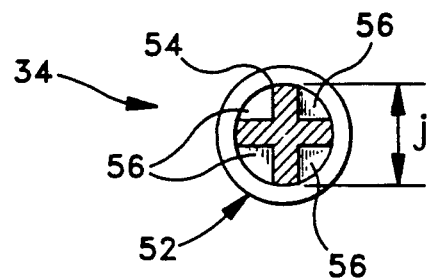
FIG. 5 is a cross-sectional view taken along line 5—5 in FIG. 4.

Plug 34 further defines a rigid tail 54 extending from head 52 to distal end 50 of the plug. Tail 54 defines an axial length "i" which in this embodiment is greater than the axial length "a" of aperture 40 through stopper 32. The length of the tail is chosen so that said head can be moved out of any position along the aperture which will block fluid flow between the aperture and the plug. The sealing portion or sealing area of the aperture comprises the length of the aperture through which the head must be moved to allow flow of fluid through the aperture. In this embodiment the sealing portion of the aperture is distance F shown in FIG. 3. Tail 54 further defines a diameter "j" which is preferably but not necessarily less than the diameters "b", "c" and "e" in aperture 40 through stopper 32. In the preferred embodiment, as shown in FIGS. 4 and 5, tail 54 of plug 34 is fluted to define a non-cylindrical cross-section having a plurality of fluid channels 56 extending axially therealong.

Figure 6:
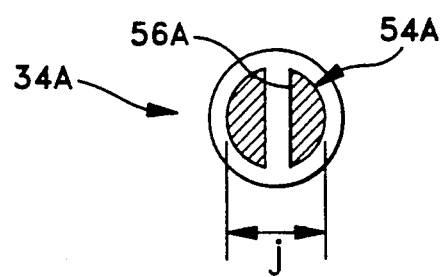
FIG. 6 is a cross-sectional view similar to FIG. 5 but showing a second embodiment of the plug.

An alternate plug 34A, as shown in FIG. 6 includes a tail 54A with a small cylindrical cross-section defining a diameter "j" which is preferably, but not necessarily, less than the diameters "b" and "c" along aperture 40 and with a longitudinally extending slot 56A defining a fluid channel.

Figure 7:
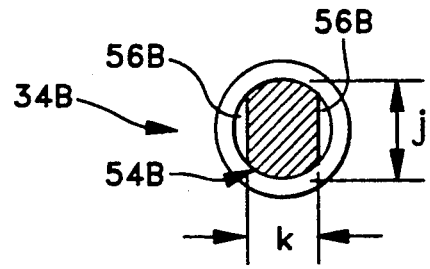
FIG. 7 is a cross-sectional view similar to FIGS. 5 and 6 but showing a third embodiment of the plug.

FIG. 7 depicts a third embodiment of a plug 34B with a tail 54B having longitudinal flats 56B on opposed sides to define fluid channels. Thus, tail 54B is of non-cylindrical cross-section and includes a major diameter "j" which is preferably, but not necessarily, less than the diameters "b", "c" and "e" in aperture 40 of stopper 32, and a minor diameter "k" which is less than the major diameter "j" and diameters "b", "c" and "e".

Figure 8:
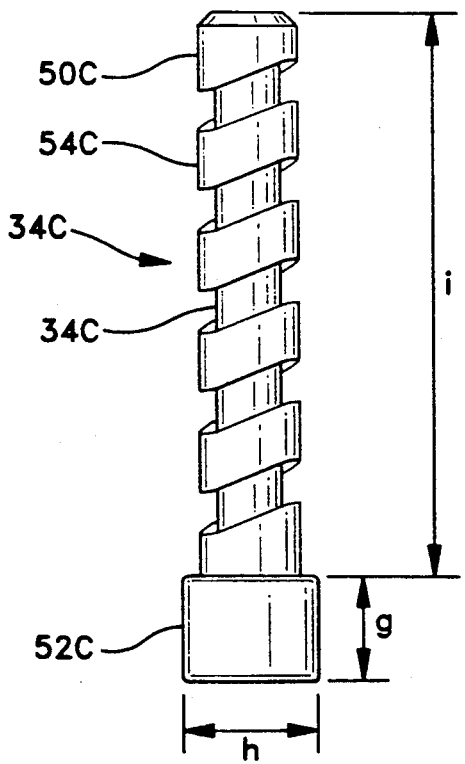
FIG. 8 is a side elevational view of an alternative embodiment of the plug element of FIG. 4.

Adverting to FIG. 8, an alternative plug 34c includes a head 52c and a tail 54c extending distally therefrom. Plug 34c has approximately the same outside dimensions as the plugs of FIGS. 5-7. A longitudinally extending slot in this embodiment is a helically shaped recess 56c running along at least a portion of the length i of the tail.

Hypodermic syringe 10 is assembled by inserting distal end 50 of tail 54 into aperture 40 of stopper 32, such that head 52 of plug 34 is engaged in seat 46 of stopper 32. Tail 54 of the plug extends from seat 46 in stopper 32, and protects beyond distal end 38 of the stopper by a distance "1", as shown in FIG. 2. Projection "1" of tail 54 beyond stopper 32 is greater than distance "f" between distal end of seat 46 and proximal end 36 of stopper 32, as shown in FIG. 3. The assembly of stopper 32 and plug 34 is then inserted into chamber 16 of the barrel. A selected dose of fluid 30 is placed into chamber 16, and plunger 28 is then inserted into proximal end 14 of the barrel. As noted above, plunger 28 and stopper 32 slidingly, but sealingly, engage the barrel 12 so that the prefilled fluid 30 is efficiently contained and isolated from syringe tip 20, needle 24 and open proximal end 14 of the barrel.

Hypodermic syringe 10 is used by initially removing needle shield 26 and axially advancing the plunger 28 toward distal end 18 of barrel 12. Slidable advancement of plunger 28 within chamber 16 of the barrel exerts pressure on fluid 30, and causes stopper 32 and plug 34 to be advanced distally within the chamber. Sufficient distal movement of stopper 32 and plug 34 will bring distal end 50 of the plug into contact with distal end 18 of the barrel. Further distal movement of plug 34 is prevented as shown in FIG. 9. Continued distal movement of plunger 28 maintains pressure on fluid 30 to be injected, and hence causes distal movement of stopper 32 independently of plug 34. Axial length "i" of tail 54 on plug 34 in this embodiment exceeds overall length "a" of aperture 40 through the stopper 32. Furthermore, projection distance "1" of tail 54 beyond stopper 32 enables head 52 to move at least distance "f" required to clear proximal end 36 of stopper 32. Thus, sufficient distal movement of stopper 32 will cause head 52 of the plug to be separated from stopper 32. The cross-sectional dimensions and configuration of tail 54 of plug 34 are such that fluid channels 56 are defined between tail 54 and stopper 32. Thus, as shown most clearly in FIG. 9, fluid 30 will be urged through channels 56 between tail 54 and stopper 32 and toward syringe tip 20 and needle 24.

Figure 11:
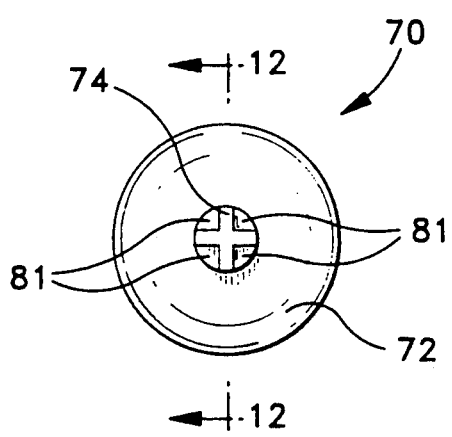
FIG. 11 is a top plan view of an alternative plug and stopper assembly for use in the present invention.
Figure 12:
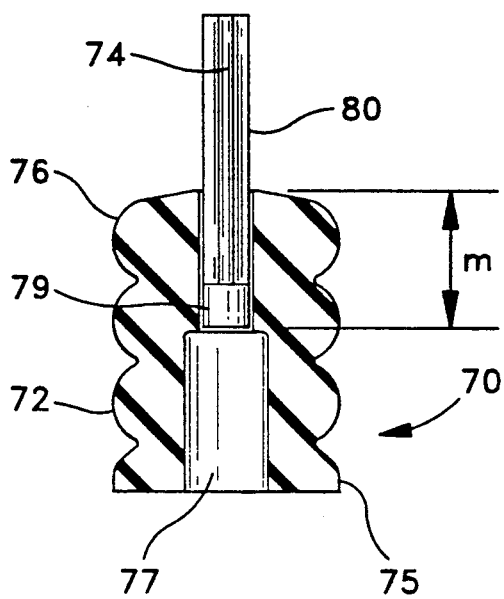
FIG. 12 is a cross-sectional view of the plug and stopper assembly of FIG. 11 taken along lines 12—12.
Figure 13:
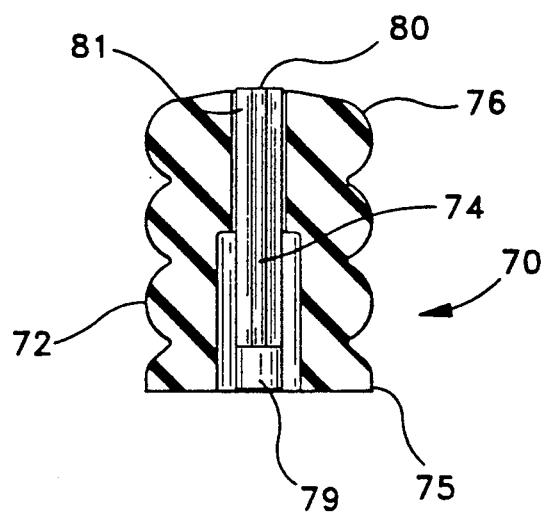
FIG. 13 is the plug and stopper assembly of FIG. 12 illustrated with the plug in a position to allow fluid to flow through the aperture of the stopper.

Adverting to FIGS. 11-13, an alternative plug and stopper assembly for use in the present invention includes a stopper 72 and a plug 74. The plug and stopper assembly 70 of this embodiment functions in the same way as the stopper and plug illustrated in the embodiments of FIGS. 1-10 and is intended for use with a syringe barrel as illustrated in FIGS. 1-2 and 9-10. The stopper includes a proximal end 75, a distal end 76 and an aperture 77 extending through the stopper from proximal end 75 to distal end 76 defining an axial length. Plug 74 includes a head 79 positioned in the aperture and a tail 80 extending distally from the head and, as illustrated in FIG. 12, projecting beyond the distal end of the stopper. The aperture includes a sealing portion along its length. In this embodiment the sealing portion has length m as illustrated in FIG. 12. The sealing portion can be the full length of the stopper or a portion of the stopper at its distal end or at its proximal end or anywhere in between wherein at least the head seals the aperture from fluid passage. The head is in fluid-tight engagement with the sealing portion. The plug and stopper assembly includes means for allowing flow between the sealing portion of the aperture and the tail so that fluid can flow through the aperture when the tail is positioned in the sealing portion as illustrated in FIG. 13. In this embodiment the tail has a fluted shape with four parallel longitudinally extending grooves which define passageways 81 when the tail is in the sealing portion. The tail in this embodiment can have all the shapes previously described such as those illustrated in FIGS. 5-8. It is also within the purview of this invention to have the sealing portion of the aperture non-circularly shaped to fit a correspondingly shaped plug head while the tail of the plug is circularly shaped so that when the tail is in the sealing portion apertures will be defined between the tail and the sealing portion. As with the previous embodiments distally directed fluid pressure in the chamber of the syringe barrel causes the stopper and the plug to move simultaneously until the tail of the plug engages the distal end of the barrel, whereafter, the fluid pressure urges the stopper distally independent of the plug to disengage said head of said plug from the sealing portion of the aperture so that the tail is positioned within the sealing portion of the aperture and to permit fluid flow between the tail and the sealing portion toward the passageway in the barrel as illustrated in FIG. 13. Here again, the tail of the plug should be long enough to move the head out of those portions of the aperture in which it occludes fluid flow.

The hypodermic syringe described and illustrated herein provides several significant advantages. In particular, fluid is effectively isolated from the syringe tip and needle until just prior to injection. The hypodermic syringe can then be used in a standard manner by merely urging plunger toward the distal end of the syringe barrel. This normal movement of the plunger will cause the unseating of the head of the plug from the sealing portion of the aperture in the stopper to enable the fluid to flow through channels formed between the tail and the sealing portion of the aperture. A smooth movement without excessive force is enabled throughout the injection procedure. A rupturable membrane is not required, and hence there is no risk of creating debris in the injectable liquid that could either block the needle cannula or pass into the patient. Furthermore, there is no need to resort to a more costly syringe barrel of non-uniform cross-section along its length or to flexible valve structures which require additional force through the injection process to keep the valve open.

While the invention has been described with respect to a preferred embodiment, it is understood that various changes can be made without departing from the scope of the invention as defined by the appended claims.

What is claimed is:

1. A hypodermic syringe comprising:
   a barrel having opposed proximal and distal ends and a fluid-retaining chamber extending therebetween, said distal end of said barrel having a passageway extending therethrough and communicating with said chamber;
   a stopper slidably disposed in fluid-tight engagement in said chamber, said stopper having opposed proximal and distal ends, an aperture extending through said stopper from said proximal end to said distal end and defining an axial length;
   a plug having a head positioned in said aperture of said stopper and a tail extending distally from said head and projecting beyond said distal end of said stopper, said aperture including a sealing portion along its length, said head being in fluid-tight engagement with said sealing portion;
   means for allowing fluid flow between said sealing portion of said aperture and said tail so that fluid can flow through said aperture when said tail is positioned within said sealing portion;
   whereby distally directed fluid pressure in the chamber causes said stopper and said plug to move simultaneously until said tail of said plug engages said distal end of said barrel, whereafter the fluid pressure urges said stopper distally independent of said plug to disengage said head of said plug from said sealing portion of said aperture so that said tail is positioned within said sealing portion of said aperture and to permit fluid flow between said tail and said sealing portion toward said passageway of said barrel.

2. The hypodermic syringe of claim 1 further comprising a plunger slidably disposed in fluidtight engagement in said barrel between said stopper and the proximal end of the barrel, said plunger being operative to exert fluid pressure for slidably urging said stopper toward the distal end of the barrel.

3. The hypodermic syringe of claim 1 wherein said sealing portion of said aperture extends from said proximal end of said stopper to said distal end of said stopper.

4. The hypodermic syringe of claim 1 wherein said sealing portion of said aperture is located in the distal end of said aperture.

5. The hypodermic syringe of claim 1 wherein said sealing portion of said aperture is located in the proximal end of said aperture.

6. The hypodermic syringe of claim 1 wherein said sealing portion of said aperture is circularly shaped and of a smaller diameter than portions of said aperture outside of said sealing portion.

7. The hypodermic syringe of claim 1 wherein said sealing portion of said aperture is circularly shaped and of a larger diameter than portions of said aperture outside of said sealing portion.

8. The hypodermic syringe of claim 1 wherein said means for allowing fluid flow between said sealing portion of said aperture and said tail includes said sealing portion of said aperture being substantially circularly shaped and said tail being substantially non-cylindrical for defining at least one fluid channel between said tail and said sealing portion.

9. The hypodermic syringe of claim 1 wherein said means for allowing fluid flow between said sealing portion of said aperture and said tail includes said sealing portion being non-circularly shaped and said tail being substantially cylindrical for defining at least one channel between said tail and said sealing portion.

10. The hypodermic syringe assembly of claim 1 wherein said tail of said plug includes at least one longitudinally extending slot along the surface of said tail.

11. The hypodermic syringe assembly of claim 1 wherein said tail of said plug includes at least one longitudinally extending flat along the surface of said tail.

12. The hypodermic syringe of claim 1 wherein said tail of said plug includes a helically shaped recess along the surface of said tail.

13. The hypodermic syringe assembly of claim 1 wherein said tail of said plug is fluted to define a plurality of channels axially aligned along the surface of the tail.

14. The hypodermic syringe of claim 1 wherein said barrel is of substantially uniform cross sectional shape between said proximal and distal ends thereof.

15. The hypodermic syringe of claim 1 wherein said plug is formed of material selected from the group consisting of thermoplastic material and hard rubber.

16. The hypodermic syringe of claim 1 wherein the stopper is formed from an elastomeric material.

17. The hypodermic syringe of claim 2 further including a volume of injectable liquid in said chamber of said barrel between said stopper and said plunger.

* * * * *